(12) United States Patent
Priou

(10) Patent No.: US 6,590,009 B1
(45) Date of Patent: Jul. 8, 2003

(54) POLYMERIZATION AND/OR CROSSLINKING METHOD UNDER ELECTRON BEAM AND/OR GAMMA RADIATION

(75) Inventor: Christian Priou, West Windsor, NY (US)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 09/762,663

(22) PCT Filed: Aug. 2, 1999

(86) PCT No.: PCT/FR99/01911

§ 371 (c)(1), (2), (4) Date: May 3, 2001

(87) PCT Pub. No.: WO00/09572

PCT Pub. Date: Feb. 24, 2000

(30) Foreign Application Priority Data

Aug. 11, 1998 (FR) .............................................. 98 10297
Jun. 11, 1999 (FR) .............................................. 99 07421

(51) Int. Cl.$^7$ .............................. C08F 2/50; G03F 7/029
(52) U.S. Cl. .............................. 522/66; 522/67; 522/99; 522/148; 522/170; 528/13; 528/26; 528/33; 528/40; 430/280.1; 430/286.1
(58) Field of Search .............................. 522/65, 66, 67, 522/99, 148, 170; 528/13, 26, 33, 40; 430/280.1, 286.1

(56) References Cited

U.S. PATENT DOCUMENTS

| | | | | | |
|---|---|---|---|---|---|
| 4,307,182 A | * | 12/1981 | Dalzell et al. | ........... | 430/270.1 |
| 5,124,235 A | * | 6/1992 | Fukui et al. | ............. | 430/281.1 |
| 5,693,688 A | * | 12/1997 | Priou | ......................... | 522/25 |
| 5,952,152 A | * | 9/1999 | Cunningham et al. | ... | 430/281.1 |
| 6,291,540 B1 | * | 9/2001 | Priou et al. | .................... | 522/31 |

FOREIGN PATENT DOCUMENTS

| | | | | |
|---|---|---|---|---|
| DE | 1 815 868 | 11/1969 | ............ | G03C/1/72 |
| EP | 0353 030 | 1/1990 | ............ | C07F/5/02 |

OTHER PUBLICATIONS

Borden D. G.: "Review of Light–Sensitive Tetraarylborates" Photographic Science and Enginering, vol. 16, No. 4, Jul. 1992 Aug. 1992, pp. 300–312, XP002041791.

* cited by examiner

Primary Examiner—Susan W. Berman

(57) ABSTRACT

The invention concerns a polymerization and/or crosslinking method under electron beam and/or gamma radiation for compositions based on monomers, oligomers and/or polymers with organic functional groups. The invention is characterized in that the crosslinking and/or polymerization is carried out in the presence of an initiator capable of being activated under electron beam and/or gamma radiation comprising a boron derivative of formula (I) M+B(Ar) 4 wherein: M+, a unit bearing a positive charge, is an alkaline metal selected among those of columns IA and IIA of the periodic table; Ar is an aromatic derivative, optionally substituted by at least a substituent selected among a fluorine radical, a chlorine radical, a linear or branched alkyl chain, which itself can be substituted by at least a fluorine atom.

13 Claims, No Drawings

POLYMERIZATION AND/OR CROSSLINKING METHOD UNDER ELECTRON BEAM AND/OR GAMMA RADIATION

This application is an application under 35 U.S.C. Section 371 of International Application Number PCT/FR99/01911 filed on Aug. 2, 1999.

The field of the invention is that of the initiating of the polymerization and/or crosslinking reactions of monomers, oligomers and/or polymers comprising reactive functional radicals capable of forming intrachain and interchain bridgings, so as to obtain a polymerized and/or crosslinked coating or composite material having a certain hardness and a certain mechanical strength.

More specifically, a subject matter of the present invention is a novel process for polymerization and/or crosslinking in the presence of novel initiators, which can be activated under an electron beam and/or gamma radiation, comprising at least one boron derivative which make possible the initiation and the progression of reactions for the formations of polymers and/or resins from substrates formed of monomers, oligomers and/or of polymers with reactive organofunctional groups.

The reactions more particularly concerned are those in which agents act as direct promoters of interchain and/or intrachain bonds. In the present case, these reactions are initiated with activation by an electron beam or by gamma radiation.

In the present description, the polymers and/or resins obtained are prepared from monomers, oligomers and/or polymers which are either (1) of organic nature, in particular solely of hydrocarbonaceous nature, or (2) of polyorganosiloxane nature and which comprise, in their structure, organofunctional groups, for example of epoxide, oxetane and/or alkenyl ether type, which react after activation by an electron beam and/or gamma radiation of the initiators according to the invention described below. In addition, it is also possible to use (3) monomers, oligomers and/or polymers with acrylic groups and/or methacrylic groups, which can be added to the polymerization medium comprising entities (1) and/or (2).

Another subject matter of the present invention is compositions comprising the polymerizable and/or crosslinkable base materials (monomers, oligomers and/or polymers), preferably of polyorganosiloxane nature, the initiators described below and, optionally, one or more additives chosen from those generally known in the applications for which these compositions are intended.

For example, these compositions can be used for the preparation of coatings on items such as solid articles or substrates, in particular a paper substrate, a fabric, a polymer film of polyester or polyolefin type, an aluminum substrate and/or a tinplate substrate.

Initiators for polymerizing and/or crosslinking monomers, oligomers and/or polymers comprising reactive organofunctional groups in their structures are disclosed in EP-0 562 897. The initiating salts of this patent represent a significant technical advance in comparison with the previously known initiators of onium salt or organometallic complex type and in particular in comparison with those in which the anion of the initiating salt is $SbF_6^-$, which is one of the only ones which is correct with regard to performance, but which presents serious operating problems because of the presence of heavy metals.

To assess the performances of initiators which can be activated under an electron beam and/or gamma radiation, their ability to polymerize a polymer or matrix is evaluated via tests, such as that of touch, or trade tests, such as that of the peel strength for nonstick coatings.

One of the essential objectives of the present invention is the development of a novel process which makes possible the polymerization and/or crosslinking of a matrix based on monomers, oligomers and/or polymers in the presence of novel initiators which can be activated by an electron beam and/or gamma radiation.

It should be noted that the initiators of this novel process have a markedly improved reactivity, in particular in comparison with those comprising an iodonium cation and/or antimony-derived anion within their structure. In addition, the use of these novel initiators does not necessarily require inert atmosphere conditions and, furthermore, they prove to be much less toxic.

An essential objective of the invention is to provide a high-performance process with respect to the greatest number of organofunctional monomers, oligomers and/or polymers which can be polymerized and/or crosslinked under activation with an electron beam and/or gamma radiation, the monomers, oligomers and/or polymers being in particular (1) of organic nature, preferably solely of hydrocarbonaceous nature, or (2) of polyorganosiloxane nature, optionally as a mixture (3) with other monomers, oligomers and/or polymers comprising acrylic and/or methacrylic groups.

Another essential objective of the invention is to provide a process which uses efficient initiators at a low concentration and which only requires small amounts of energy (expressed in kilograys) for carrying out the polymerization and/or crosslinking. For this reason, the industrial processes using initiators of these types prove to be particularly economical.

Another essential objective of the invention is to provide a high performance process in which the polymerization and/or crosslinking reactions are carried out at high rates. Thus, the duration of activation under an electron beam and/or gamma radiation is very short and is generally approximately less than one second and of the order of a few tenths of a second for the preparation of very thin coatings. Of course, the polymerisation/crosslinking time may vary according to the number of electron beam and/or gamma radiation sources, the duration of the activation and the distance between the composition and the activating beam (s). Thus, the process according to the invention can be employed with industrial devices in which the rate of forward progression of the composition to be crosslinked on a backing strip is very high.

Another objective of the invention is to provide compositions comprising organofunctional monomers, oligomers and/or polymers which can be crosslinked via initiators which can be activated by an electron beam and/or gamma radiation. The optimum performances are obtained in particular with compositions comprising organofunctional monomers, oligomers and/or polymers of polyorganosiloxane nature.

Another objective of the invention is to provide compositions of this type which can be used just as easily in a thin layer, the thickness of which lies, for example, in the range from 0.1 to 10 µm, as in a thicker layer, the thickness of which lies, for example, in the range from a value of greater than 10 micrometers to several centimeters.

Another objective of the invention is to provide compositions of this type for the preparation of composite materials.

These various objectives are achieved by the invention, which relates first of all, in its first subject matter, to a novel process for crosslinking and/or polymerizing, under an electron beam and/or gamma radiation, compositions based on monomers, oligomers and/or polymers comprising organofunctional groups, in which process the crosslinking and/or polymerization is carried out in the presence of an initiator which can be activated by an electron beam and/or gamma radiation comprising a boron derivative of formula $M^+ B(Ar)_4^-$ (I) where:

$M^+$, an entity carrying a positive charge, is chosen from an alkali metal from columns IA and IIA of the Periodic Classification (CAS version), Ar is an aromatic derivative, optionally substituted by at least one substituent chosen from a fluorine radical, a chlorine radical or a linear or branched alkyl chain, which can itself be substituted by at least one electron-withdrawing group, such as $C_nF_{2n+1}$, with n being between 1 and 18 (for example: $CF_3$, $C_3F_7$, $C_2F_5$ or $C_8F_{17}$), F and $OCF_3$.

According to an alternative form of the invention, M is chosen from lithium, sodium, cesium and/or potassium.

By way of example, the boron derivative of the initiator according to the invention is of formula:

$LiB(C_6F_5)_4$, $KB(C_6F_5)_4$, $KB(C_6H_3(CF_3)_2)_4$ and $CsB(C_6F_5)_4$.

The initiators according to the invention can be employed, as they are obtained on conclusion of their preparation process, for example in the solid or liquid form, or in solution in at least one appropriate solvent, in monomer, oligomer and/or polymer compositions which are intended to be polymerized and/or crosslinked. In the context of the invention, the term "solvent" encompasses the products which dissolve the solid initiators and the products which dilute the liquid or solid initiators.

Preferably, the initiators are generally employed in solution in a solvent. The proportions by weight of the initiator or initiators, on the one hand, to the solvent, on the other hand, are between 0.1 and 99 parts per 100 parts of solvent and preferably from 10 to 50 parts.

The solution is subsequently used to prepare a bath with the monomer(s), oligomer(s) and/or polymer(s) comprising crosslinkable functional groups, such that the concentration of the initiator or initiators present is between 0.01 and 5% by weight in said bath and preferably between 0.05 and 0.5%.

The solvents which can be used for the initiators are very numerous and highly varied and are chosen according to the initiator used and the other constituents of the composition of the invention. In general, the solvents can be alcohols, esters, ethers, ketones and/or silicones.

The silicones used to dilute and/or dissolve the initiators can be similar or identical to the monomers, oligomers and/or polymers constituting the crosslinkable and/or polymerizable composition.

The alcohols commonly employed are para-tolyl-ethanol, isopropylbenzyl alcohol, benzyl alcohol, methanol, ethanol, propanol, isopropanol and butanol. The ethers commonly used are 2-methoxyethanol, 2-ethoxyethanol and diethylene glycol. The usual esters are dibutyl maleate, dimethyl ethylmalonate, methyl salycilate, dioctyl adipate, butyl tartrate, ethyl lactate, n-butyl lactate and isopropyl lactate. Other solvents which can be used for the bath of the initiator coming within the other categories of solvents mentioned above are acetonitrile, benzonitrile, acetone, cyclohexanone and tetrahydrofuran.

In addition, among the solvents which can be used for dissolving the initiator or initiators, some types of proton-donating organic solvents and some types of hydroxylated carboxylic acid esters have the properties also of significantly improving their performance with respect to reactivity and kinetics.

Mention will be made, among these types of solvents, referred to as reactive diluents, of:

(1) benzyl alcohol of following general formula (II):

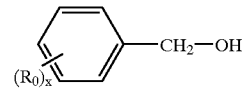

in which:
the $R_0$ groups are identical or different and represent an electron-donating or electron-withdrawing group chosen from linear or branched alkyls comprising 1 to 12 carbon atoms, linear or branched alkoxyls comprising 1 to 12 carbon atoms, cycloalkyls, cycloalkoxyls or optionally substituted aryls, preferably substituted by halogens or radicals such as, for example, $NO_2$,
x is an integer between 0 and 5.

(2) hydroxylated carboxylic acid esters which are liquid at ambient temperature (23° C.), of general formula:

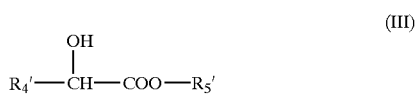

(III)

in which:
the $R_4'$ and $R_5'$ symbols are identical or different and represent:
a linear or branched $C_1-C_{10}$ alkyl radical, optionally substituted by a linear or branched $C_1-C_4$ alkoxy group,
a $C_4-C_{10}$ cycloalkyl radical, optionally substituted by one or more linear or branched $C_1-C_4$ alkyl or alkoxy group(s),
a $C_5-C_{12}$ aryl radical, optionally substituted by one or more linear or branched $C_1-C_4$ alkyl or alkoxy group(s), and/or
an aralkyl or aroxyalkyl radical where the aryl part is a $C_5-C_{12}$ group optionally substituted by one or more linear or branched $C_1-C_4$ alkyl or alkoxy group(s) and the alkyl part is a linear or branched $C_1-C_4$ group,
it being additionally possible for the $R_4'$ symbol to represent:
a linear or branched $C_1-C_{15}$ alkoxy radical, and/or
a $C_4-C_{10}$ cycloalkyloxy radical, optionally substituted by one or more linear or branched $C_1-C_4$ alkyl or alkoxy group(s).

According to a first other advantageous provision of the invention taken in its first subject matter, the polymerizable and/or crosslinkable composition is based on monomer(s) and/or oligomer(s) and/or polymer(s) of polyorganosiloxane nature and/or of organic nature, in particular of hydrocarbonaceous nature.

According to a second other advantageous provision of the invention taken in its first subject matter, the polymerizable and/or crosslinkable composition is based on monomer(s) and/or oligomer(s) and/or polymer(s) of polyorganosiloxane nature and/or of organic nature, in particular of hydrocarbonaceous nature, and additionally comprises monomers, oligomers and/or polymers comprising organofunctional groups of acrylate kind and in particular epoxidized acrylates, polyester glycerol acrylates, multifunctional acrylates, urethane acrylates, polyether acrylates, polyester acrylates, unsaturated polyesters or acrylic acrylates.

These acrylic entities, optionally as a mixture, which can be used with monomer(s) and/or oligomer(s) and/or polymer(s) of polyorganosiloxane nature and/or of organic nature, are preferably chosen from the following entities: trimethylolpropane triacrylate, tripropylene glycol diacrylate, glycidylpropyl triacrylate, pentaerythritol triacrylate, dipentaerythritol pentaacrylate, ethoxylated pentaerythritol tetraacrylate, trimethylolpropane ethoxylate triacrylate, bisphenol A ethoxylate diacrylate, tripropylene glycol diacrylate, triethylene glycol diacrylate, tetraethylene glycol diacrylate, polyether acrylates, polyester acrylates (for example the product EBECRYL 810 from UCB-Radcure) and epoxy acrylates (for example, the product EBECRYL 600 from UCB-Radcure).

According to another of the aspects of the present invention, the invention relates, in its second subject matter, to compositions comprising at least one matrix based on monomer(s), on oligomer(s) and/or on polymer(s) of polyorganosiloxine nature comprising polymerization and/or crosslinking organofunctional groups and an effective amount of at least one initiator of the type of those in accordance with the invention described above, optionally a polymerization and/or crosslinking accelerator and, optionally again, one or more additives chosen from those generally known in the applications for which these compositions are intended.

The term "effective amount of initiator" is understood to mean, in accordance with the invention, the amount sufficient to initiate the polymerization and/or the crosslinking. This amount is generally between 0.01 and 1 parts by weight, generally between 0.05 and 0.5 parts by weight, for polymerizing and/or crosslinking 100 parts by weight of the matrix.

According to a third advantageous provision of the invention taken in its first subject matter and a first advantageous provision of the invention-taken in its second subject matter, the monomer(s) and/or oligomer(s) and/or polymer(s) are of polyorganosiloxane nature, are composed of units of formula (IV) and are terminated by units of formula (V) or are cyclic and are composed of units of formula (IV) represented below:

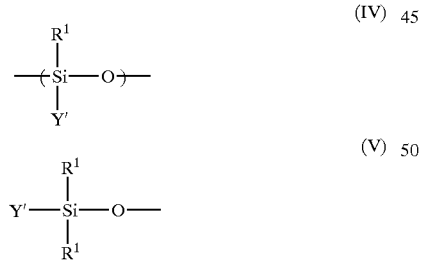

in which:
the $R^1$ symbols are alike or different and represent:
a linear or branched alkyl radical comprising 1 to 8 carbon atoms which is optionally substituted by at least one halogen, preferably fluorine, the alkyl radicals being methyl, ethyl, propyl, octyl and 3,3,3-trifluoropropyl,
an optionally substituted cycloalkyl radical comprising between 5 and 8 cyclic carbon atoms,
an aryl radical comprising between 6 and 12 carbon atoms which can be substituted, preferably phenyl or dichlorophenyl,
an aralkyl part having an alkyl part comprising between 5 and 14 carbon atoms and an aryl part comprising between 6 and 12 carbon atoms, which is optionally substituted on the aryl part by halogens, alkyls and/or alkoxyls comprising 1 to 3 carbon atoms,
the Y' symbols are alike or different and represent:
the $R^1$ group,
a hydrogen radical,
and/or a crosslinkable organofunctional group, preferably an epoxyfunctional and/or vinyloxyfunctional group, connected to the silicon of the polyorganosiloxane via a divalent radical comprising from 2 to 20 carbon atoms which can comprise at least one heteroatom, preferably oxygen,
and at least one of the Y' symbols representing a crosslinkable functional organic group.

According to an advantageous alternative form of the invention, the polyorganosiloxanes used comprise from 1 to 10 organofunctional groups per macromolecular chain. For an epoxyfunctional group, this corresponds to epoxide levels varying from 20 to 2 000 molar meq./100 g of polyorganosiloxane.

The linear polyorganosiloxanes can be oils with a dynamic viscosity at 25° C. of the order of 10 to 10 000 mPa·s at 25° C., generally of the order of 50 to 5 000 mPa·s at 25° C. and more preferably still of 100 to 600 mPa·s at 25° C. or gums exhibiting a molecular mass of the order of 1 000 000.

When they are cyclic polyorganosiloxanes, the latter are composed of units (IV) which can be, for example, of the dialkylsiloxy or alkylarylsiloxy type. These cyclic polyorganosiloxanes exhibit a viscosity of the order of 1 to 5 000 mPa·s.

Mention may be made, as examples of divalent radicals connecting an organofunctional group of the epoxy type, of those included in the following formulae:

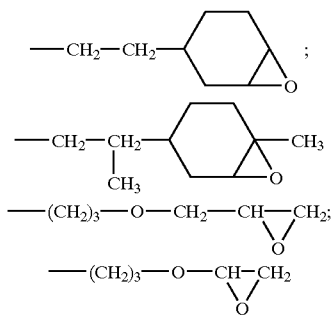

As regards the organofunctional groups of the alkenyl ether type, mention may be made of those present in the following formulae:

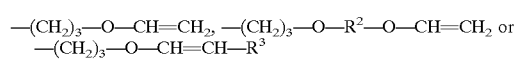

in which
$R^2$ represents:
an optionally substituted linear or branched $C_1$–$C_{12}$ alkylene radical,
or a $C_5$–$C_{12}$ arylene radical, preferably a phenylene radical, which is optionally substituted, preferably by one to three $C_1$–$C_6$ alkyl groups,
$R^3$ represents a linear or branched $C_1$–$C_6$ alkyl radical.

The dynamic viscosity at 25° C. of all the silicones considered in the present description can be measured using a Brookfield viscometer according to the AFNOR Standard NFT 76 102 of February 1972.

According to a second other advantageous provision of the invention taken in its second subject matter, the matrix of the polymerizable and/or crosslinkable composition is based on monomer(s) and/or oligomer(s) and/or polymer(s) of polyorganosiloxane nature and of organic nature, in particular of hydrocarbonaceous nature.

According to a third other advantageous provision of the invention taken in its second subject matter, the matrix of the polymerizable and/or crosslinkable composition is based on monomer(s), and/or oligomer(s) and/or polymer(s) of polyorganosiloxane nature and optionally of organic nature, in particular of hydrocarbonaceous nature, and additionally comprises monomers, oligomers and/or polymers comprising organofunctional groups of acrylate kind and in particular epoxidized acrylates, polyester glycerol acrylates, multifunctional acrylates, urethane acrylates, polyether acrylates, polyester acrylates, unsaturated polyesters or acrylic acrylates.

These acrylic entities, optionally as a mixture, which can be used with monomer(s) and/or oligomer(s) and/or polymer(s) of polyorganosiloxane nature and/or of organic nature, are preferably chosen from the following entities: trimethylolpropane triacrylate, tripropylene glycol diacrylate, glycidylpropyl triacrylate, pentaerythritol triacrylate, dipentaerythritol pentaacrylate, ethoxylated pentaerythritol tetraacrylate, trimethylolpropane ethoxylate triacrylate, bisphenol A ethoxylate diacrylate, tripropylene glycol diacrylate, triethylene glycol diacrylate, tetraethylene glycol diacrylate, polyether acrylates, polyester acrylates (for example the product Ebecryl 810 from UCB-Radcure) and epoxy acrylates (for example, the product Ebecryl 600 from UCB-Radcure).

It should be remembered that, in the present description, the expression "acrylic" encompasses compounds comprising the functional group of $CH_2=CH-COO-$ type or of $CH_2=C(CH_3)-COO-$ type.

Conventionally, the compositions according to the invention can additionally comprise one or more additives chosen according to the final application targeted.

When the polymerizable and/or crosslinkable composition is based on at least one organic entity, as a mixture optionally with monomers, oligomers and/or polymers of acrylic nature, the additives can in particular be compounds, optionally in the form of polymers, comprising mobile hydrogens, such as alcohols, glycols and polyols, of use in improving the flexibility of the cured material after polymerization and/or crosslinking; mention may be made, for example, of polycaprolactonepolyols, in particular the polymer obtained from 2-ethyl-2-(hydroxymethyl)-1,3-propanediol and 2-oxepanone, such as the product Tone Polyol-301 sold by Union Carbide or the other commercial polymers Tone Polyol 201 and Tone Polyol 12703 from Union Carbide. In addition, in this case, mention may be made, as additives, of diacids with a long alkyl chain, fatty esters of unsaturated acids which may or may not be epoxidized, for example epoxidized soybean oil or epoxidized linseed oil, the epoxidized 2-ethylhexyl ester, 2-ethylhexyl epoxystearate or octyl epoxystearate, epoxidized acrylic esters, epoxidized acrylates of soybean oil, epoxidized acrylates of linseed oil, polypropylene glycol diglycidyl ether, aliphatic epoxides with a long chain, and the like.

They can also be, whatever the nature of the polymerizable matrix, for example: fillers, such as in particular milled synthetic (polymer) or natural fibers, calcium carbonate, talc, clay, titanium dioxide, or precipitated or fumed silica; soluble dyes; oxidation and corrosion inhibitors; organosilicon or non-organosilicon adhesion modulators; fungicidal, bactericidal or antimicrobial agents; and/or any other material which does not interfere with the activity of the initiator.

For the use of the initiators according to the invention, various sources of irradiation by electron bombardment can be used to carry out the polymerization and/or crosslinking of the monomers, oligomers and/or polymers. It should be noted that the reaction mechanisms involved are of different types, one of the type identified involving cationic entities.

Mention will be made, as examples of devices which can be used, of those of pulsed electron beam type (Scanned Electron Beam Accelerator) and those of electron curtain beam type (Electron Curtain Accelerator). A pulsed electron beam device is used in the following examples and tests. By way of an alternative, gamma radiation can be used as irradiation source for the polymerization and/or crosslinking.

The resins obtained from the process or composition according to the invention can be used for the manufacture of a coating and/or composite materials. By way of nonlimiting examples, the coating prepared can be a varnish, an adhesive coating, a nonstick coating and/or an ink.

EXAMPLE AND TESTS

The following 2 series of preparations and tests A and B are given by way of illustration. They will make it possible in particular to achieve a better understanding of the invention and to emphasise all its advantages and to perceive some of its alternative embodiments. They demonstrate in particular the improved reactivity under an electron beam of the initiators according to the invention with respect to the those of the prior art, in particular those based on iodonium salts.

The initiators tested are found in Table I below. These initiators were evaluated under an electron beam in the presence of the epoxysilicone. The epoxysilicone is a (1,2-epoxy-4-ethylcyclohexyl)-polydimethylsiloxane of formula (VI) in which a and b have the mean values of 7 and 83 respectively.

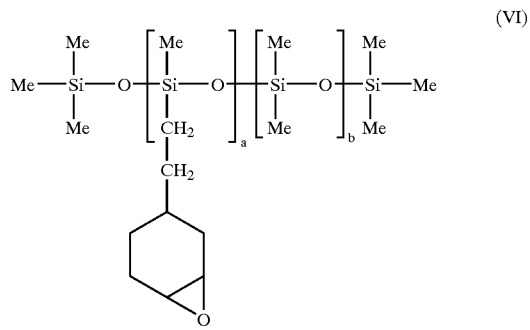

The initiators tested are listed below in Table I.

TABLE I

| Initiators used according to the invention: | | | |
|---|---|---|---|
| A1 | $LiB(C_6F_5)_4$ | A2 | $KB(C_6F_5)_4$ |
| A3 | $CsB(C_6F_5)_4$ | A4 | $KB[(C_6H_3(CF_3)_2]_4$ |

Comparative tests:

T1 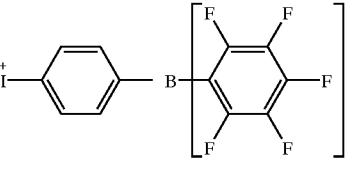

T2 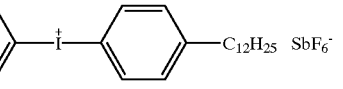

T3 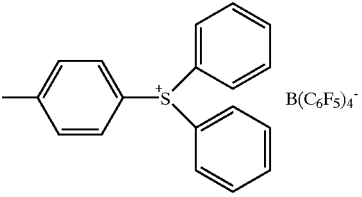

The initiator is mixed with the appropriate solvent. This solution is then added to the epoxysilicone matrix (VI). The initiator-solvent mixtures and the formulations with the epoxysilicone (VI) are given below in Table 2 and 3 respectively.

The compositions C1, C2, C3, C5 and C8 comprise the same molar concentration of initiator, namely $0.197 \times 10^{-3}$ mol/100 g of epoxysilicone.

The composition C6 is twice as rich in initiator, because of the lower reactivity of this iodonium salt, i.e. $0.586 \times 10^{-3}$ mol/100 g of silicone resin.

The composition C7 comprises half as much initiator as the other compositions, namely $0.097 \times 10^{-3}$ mol/100 g of epoxysilicone, so as to exemplify the very high reactivity of the salts of the invention.

TABLE 2

| Initiator | Solvent | % by weight of initiator in the solvent |
|---|---|---|
| A1 | Isopropanol | 16.9 |
| A2 | Isopropanol | 17.7 |
| T1 | Isopropanol | 25 |
| T2 | Dodecylbenzene + mixture of alkyl glycidyl ethers | 50 |
| T3 | Butyl lactate | 25.9 |
| A4 | Isopropanol | 10.6 |
| A3 | Acetone | 20 |

As the initiator T2 exhibits a very low intrinsic solubility in the epoxysilicone-based systems, only the formulation in Table 2 resulted in crosslinked coatings.

The other initiators in Table 2 are compatible with numerous conventional solvents and thus make possible the development of numerous and different formulations.

TABLE 3

| Composition | Initiator | Initiator solution mass (g) | Epoxysilicone mass (g) | Concentration of initiator in the composition (wgt %) |
|---|---|---|---|---|
| C1 | A1 | 0.935 | 100 | 0.13 |
| C2 | A2 | 0.941 | 100 | 0.14 |
| C3 | T1 | 1.00 | 100 | 0.2 |
| C4 | T1 | 0.5 | 100 | 0.1 |
| C5 | T3 | 1.01 | 100 | 0.21 |
| C6 | T2 | 1 | 100 | 0.5 |
| C7 | A4 | 0.887 | 100 | 0.085 |
| C8 | A3 | 0.96 | 100 | 0.16 |

All the compositions are clear, with the exception of the formulation C5, which is slightly hazy. After 22 hours at ambient temperature, the viscosity of the compositions C1, C2, C7 and C8 has not changed, which shows the excellent thermal stability of the initiators claimed.

A2—Coating

Each of the compositions is coated using a Meyer rod on an untreated polyester 6001 substrate (thickness of 36 microns). The thickness deposited is of the order of 2 microns.

A3—Treatment of the Coated Film Under an Electron Beam

The film is treated under a 175 kV electron beam with a Curtain CB150 electron bombardment device sold by Energy Science. Treatments at doses of between and 50 kGray are carried out at a constant intensity of I=3 mA. Beyond these values, the intensity is adjusted in order to achieve the desired dose.

A4—Evaluation of the Crosslinking by the Touch Test

In these tests, the goal is the minimum dose necessary (unit: kiloGray), that is to say the minimum energy necessary, to obtain a system which is dry to the touch after treatment.

To do this, the system coated with silicone is placed after crosslinking on a flat and rigid surface, the silicone being on the upper face. A mark is made with the finger and then the mark thus made is examined by eye, preferably in low-angled light. The presence of a mark made with the finger reveals a lack of crosslinking.

The minimum doses to be applied in order to obtain a satisfactorily crosslinked coating or substrate, that is to say not exhibiting a mark, are given in Table 4. A control composition TO not comprising initiator was evaluated in order to confirm that the epoxysilicone did not crosslink under an electron beam in the absence of an initiator.

TABLE 4

| Composition | Minimum dose (kGy) | Intensity I (mA) |
|---|---|---|
| T0 | >80 | 3 |
| C1 | 30 | 3 |
| C2 | <1 | 0.3 |
| C3 | 20 | 3 |
| C5 | 30 | 3 |
| C6 | 30 | 3 |
| C7 | 5 | 1 |
| C8 | <1 | 0.3 |

The initiators A1, A2, A3 and A4 of the invention, although.used at lower concentrations than the known initiators T1, T2 and T3, exhibit a much higher reactivity than the latter.

A5—Evaluation of the Peel Strength

In these tests, used in the context of paper adhesive resistance, the peel strength necessary to detach an adhesive-comprising frontal substrate applied to a crosslinked silicone substrate obtained from each composition is evaluated.

a) Application of Adhesive

The application of adhesive to the crosslinked silicone coatings or substrates obtained after treatment with an electron beam is carried out 15 minutes after the irradiation with two adhesive tapes. The two standard test adhesive tapes used are Tesa 4970, sold by Beiersdorf, or Rhodotak 338 J, sold by Rhodia.

The adhesive-comprising complexes thus prepared are stored under a pressure of 70 g/cm$^2$ (corresponding to the pressure exerted in a machine outlet spool) at a relative humidity of 53–54% at different temperatures.

b) Ageing

Subsequently, two types of temperature-accelerated ageing are carried out for each adhesive-comprising complex:

20 h at 70° C., according to the Finat 10 method 7 days at 70° C.

These accelerated ageings are carried out in order to simulate the change in the adhesive-comprising complex during natural storage. The stability of the peel strengths over time is an essential property in the context of the paper adhesive resistance application.

c) Measurement of the Peel Strengths

This strength is expressed in g/cm and is measured using an Instron 4301 dynamometer with the following specifications:

tension of 0.5 to 5 kN, traverse rate of 0.5 to 500 mm/min.

The peel strengths are measured with an angle between the silicone substrate and the adhesive of 180° and at the rate of 0.3 m/min.

The compositions described above were crosslinked at various irradiation doses. The results obtained in Tests 1 to 16 are described in Tables 4 and 5.

According to the data in the two Tables 5 and 6, it is clearly apparent that the use of the initiators A1, A2, A3 and A4 according to the invention makes it possible to obtain satisfactorily crosslinked coatings under advantageous economic conditions since the energy necessary to manufacture these coatings is much lower in comparison with that required for the initiators cited by way of comparison.

The stability of the peel strengths during the accelerated ageings is better with the initiators of the invention, in particular with the initiator A3, which leads to excellent results, although the concentration of the initiator used is half that in examples E1, E2, E3, E4, E7 or E8.

It is also noticed that different levels of peel strengths are achieved by varying the nature of the initiator and the dose applied, without the stability of the peel strengths in these cases being detrimentally affected.

TABLE 5

Compositions according to the invention

| Test No. | Composition | Dose (kGray) | Peel strengths (g/cm) | | | |
|---|---|---|---|---|---|---|
| | | | TESA 4970 | | RHODOTAK 338 J | |
| | | | 20 h/70° C. | 7 d/ 70° C. | 20 h/ 70° C. | 7 d/ 70° C. |
| E1 | C1 | 30 | 20.2 | 34.2 | 18 | Nm |
| E2 | C1 | 40 | 14.3 | 18.6 | 10 | Nm |
| E3 | C2 | 5 | 17.1 | 26.2 | 6.1 | Nm |
| E4 | C2 | 10 | 14.2 | 25.0 | 11.2 | Nm |
| E5 | C7 | 5 | 12.1 | 12.4 | 4.0 | 4.1 |

TABLE 5-continued

Compositions according to the invention

| Test No. | Composition | Dose (kGray) | Peel strengths (g/cm) | | | |
|---|---|---|---|---|---|---|
| | | | TESA 4970 | | RHODOTAK 338 J | |
| | | | 20 h/70° C. | 7 d/ 70° C. | 20 h/ 70° C. | 7 d/ 70° C. |
| E6 | C7 | 10 | 11.6 | 7.3 | 3.8 | 6.3 |
| E7 | C8 | 1 | 6.0 | 6.7 | 12.0 | 4.3 |
| E8 | C8 | 10 | 20.7 | 20.4 | 9.6 | 3.8 | nm: not measured

TABLE 6

Comparative tests

| Test No. | Composition | Dose (kGray) | Peel strengths (g/cm) | | | |
|---|---|---|---|---|---|---|
| | | | TESA 4970 | | RHODOTAK 338 J | |
| | | | 20 h/70° C. | 7 d/ 70° C. | 20 h/ 70° C. | 7 d/ 70° C. |
| E9 | C3 | 15 | 7.5 | 28 | 7.8 | 14.1 |
| E10 | C3 | 20 | 24 | 32 | 14.5 | 4.6 |
| E11 | C4 | 20 | 68 | 74 | 9 | Nm |
| E12 | C4 | 40 | 33 | 30 | 30 | Nm |
| E13 | C5 | 30 | 19.6 | 10.0 | 3.1 | Nm |
| E14 | C5 | 35 | 17.8 | 11.3 | 4.6 | Nm |
| E15 | C6 | 30 | 20 | 13.1 | 12.5 | Zipping |
| E16 | C6 | 40 | 9.7 | 17.9 | 6.5 | 5 | nm: not measured

B1—Preparation of the Formulations to be Coated

The initiators used are A2 and T1.

Each initiator is dissolved with isopropanol. This solution is then added to the epoxysilicone (IV). The initiator-solvent mixtures and the formulations with the epoxysilicone are given below in Table 7 respectively. The compositions obtained are clear. For the composition A2, the % by weight of initiator in the solvent is 11.8 and, for the composition T1, the % by weight of initiator in the solvent is 16.7.

TABLE 7

| Composition | Initiator | Initiator solution mass (g) | Epoxysilicone mass (g) | Concentration of initiator per 100 g of epoxysilicone × 10$^{-4}$ mol |
|---|---|---|---|---|
| C9 | A2 | 1.2 | 100 | 1.97 |
| C10 | T1 | 1.2 | 100 | 1.97 |

B2—Coating

Each composition is coated on glassine paper (Ahlstrom, reference Silcote 2010) using a coating smooth roller.

The glassine paper is stored on a drum on an industrial-scale device. The mechanical rate of forward progression of the paper strip can be varied and is between 10 and 1 000 m/min.

The glassine paper is coated with a composition using a smooth roller. The amount is shown in the table for each test (E17 to E28).

B3—Treatment of the Coated Paper Under an Electron Beam

The paper coated surface is subsequently irradiated under an electron beam generated under an excitation voltage of 150 kilovolts. The dose D for each test is given in Table 8.

D=k(I/V) in kgray.

k=factor related to unity.

V=rate of forward progression.

I=intensity of the current.

B4—Evaluation of the Crosslinking by the Touch Test

The crosslinking for each test is evaluated. To do this, the glassine paper coated with the crosslinked silicone composition is placed on a flat rigid surface, the silicone composition being on the upper face.

A mark is made with a finger and then the mark thus made is examined by eye, preferably in low-angled light. The presence of a mark made with the finger reveals a lack of crosslinking. The results are given [lacuna] Table 8.

B5—Evaluation of the Peel Strength

The peel strength necessary to detach an adhesive-comprising frontal substrate applied to the glassine paper coated with the crosslinked silicone composition obtained from each composition C9 and C10 is evaluated.

a) Application of Adhesive

The application of adhesive to the crosslinked silicone papers obtained after treatment with an electron beam is carried out 15 minutes after irradiation with the two adhesive tapes. The standard test adhesive tape used is the Tesa 4970 tape from Beiersdorf.

The adhesive-comprising complexes thus prepared are stored under a pressure of 70 g/cm² (corresponding to the pressure exerted in a machine outlet spool) at a relative humidity of 53–54% at different temperatures.

b) Ageing

Subsequently, various types of ageing tests are carried out for each adhesive-comprising complex:

(i) 20 h at 20° C. according to the Finat 3 method.

(ii) 20 h at 70° C. according to the Finat 10 method.

(iii) 7 days at 70° C.

(iv) 1 month.

(v) 3 months.

The accelerated ageings (i) to (iii) are carried out to simulate the change in the adhesive-comprising complex during natural storage. The stability of the peel strengths over time is an essential property in the context of the paper adhesive resistance application.

The results of the ageing tests are given [lacuna] Table 8.

What is claimed is:

1. A process for crosslinking or polymerizing, under an electron beam or gamma radiation, compositions comprising monomers, oligomers or polymers with organofunctional groups, comprising the step of carrying out a crosslinking or a polymerization by exposure to electron beam or gamma radiation in the presence of an initiator which is activated under an electron beam or gamma radiation, said initiator comprising a boron compound of formula $M^+ B(Ar)_4^-$ (I), wherein:

$M^+$ is an alkali metal from columns IA and IIA of the Periodic Classification (CAS version), Ar is an aromatic compound, optionally substituted by at least one substituent selected from the group consisting of a fluorine radical, a chlorine radical and a linear or branched alkyl chain, wherein the alkyl chain of Ar is substituted by at least one electron-withdrawing group selected from the group consisting of F, $OCF_3$ and $C_nF_{2n+1}$, wherein n is between 1 and 18.

2. A process according to claim 1, wherein M is lithium, sodium, cesium or potassium.

3. A process according to claim 1, wherein the boron compound is $LiB(C_6F_5)_4$, $KB(C_6F_5)_4$, $KB(C_6H_3(CF_3)_2)_4$ or $CsB(C_6F_5)$.

4. A process according to claim 1, wherein the monomers, oligomers or polymers are organic or polyorganosiloxane compounds, the organofunctional groups being epoxide, oxetane, alkenyl ether or acrylic groups.

5. A process according to claim 4, wherein the polymers are polyorganosiloxanes comprising units of formula (IV) terminated by units of formula (V) or are cyclic polyorganosiloxanes comprising units of formula (IV):

TABLE 8

| Compositions | Rate (m/min) | Dose D (kgray) | Test | Material deposition (g/m²) | Touch test | Finat 3 g/cm | Finat 10 g/cm | 7 days at 70° C. g/cm | Natural ageing g/cm | |
|---|---|---|---|---|---|---|---|---|---|---|
| | | | | | | | | | 1 MONTH | 3 MONTHS |
| C9 | 200 | 20 | E17 | 1.51 | No | 27 | 48 | 84 | 35 | 51.5 |
| | | 10 | E18 | 1.47 | No | 20.8 | 27.5 | 42 | 23.6 | 36.8 |
| | | 5 | E19 | 1 | No | 45 | 115 | 156 | 122 | 107 |
| | 500 | 20 | E20 | 1.24 | No | 53 | 69 | 115 | 76 | 69.5 |
| | | 10 | E21 | 1.49 | No | 43 | 59 | 67 | 47 | 42.2 |
| | | 5 | E22 | 1.41 | No | 48 | 89 | 88 | 123 | 90.6 |
| C10 | 200 | 20 | E23 | 1.35 | No | 55 | 144 | 184 | 99 | 119 |
| | | 20 | E24 | 1.4 | Yes | 62 | tearing | tearing | 145 | 203 |
| | | 5 | E25 | 1.35 | Yes | not polymerized | not polymerized | not polymerized | not polymerized | not polymerized |
| | 500 | 20 | E26 | 1.32 | Yes | 44 | tearing | 166 | 166 | 201 |
| | | 10 | E27 | 1.35 | Yes | not polymerized | not polymerized | not polymerized | not polymerized | not polymerized |
| | | 5 | E28 | 1.43 | Yes | not polymerized | not polymerized | not polymerized | not polymerized | not polymerized |

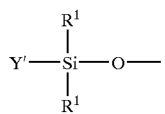

(V)

wherein:
R¹ is the same or different and represents:
a linear or branched alkyl radical having 1 to 8 carbon atoms which is optionally substituted by at least one halogen,
an optionally substituted cycloalkyl radical comprising between 5 and 8 cyclic carbon atoms,
an aryl radical comprising between 6 and 12 carbon atoms which can be substituted, or
an aralkyl radical having an alkyl part comprising between 5 and 14 carbon atoms and an aryl part comprising between 6 and 12 carbon atoms, which is optionally substituted on the aryl part by halogens, alkyls or alkoxyl groups comprising 1 to 3 carbon atoms, Y' is the same or different and represents:
the R¹ group,
a hydrogen radical, or
a crosslinkable organofunctional group, bonded to the silicon of the polyorganosiloxane via a divalent radical comprising from 2 to 20 carbon atoms, optionally bearing at least one heteroatom, and
at least one of the Y' symbols represents a crosslinkable functional organic group.

6. A process according to claim 5, wherein at least one of the R¹ symbols represents a phenyl, tolyl or dichlorophenyl radical.

7. A process according to claim 5, wherein the crosslinkable composition further comprises monomers, oligomers or polymers comprising acrylate groups.

8. A process according to claim 7, wherein the monomers, oligomers or polymers are epoxidized acrylates, polyester glycerol acrylates, multifunctional acrylates, urethane acrylates, polyether acrylates, polyester acrylates, unsaturated polyesters or acrylic acrylates.

9. A composition polymerizable or crosslinkable under an electron beam or gamma radiation, comprising oligomers or polymers of polyorganosiloxane comprising polymerizable or crosslinkable organofunctional groups and at least one initiator comprising a boron compound of formula $M^+B(Ar)_4^-$ (I), wherein:
$M^+$ is an alkali metal from columns IA and IIA of the Periodic Classification (CAS version),
Ar is an aromatic compound, optionally substituted by at least one substituent selected from the group consisting of a fluorine radical, a chlorine radical, a linear alkyl chain, and a branched alkyl chain, wherein the alkyl chain of Ar is substituted by at least one electron-withdrawing group selected from the group consisting of F, $OCF_3$ and $C_nF_{2n+1}$, wherein n is between 1 and 18.

10. A composition according to claim 9, wherein the polymers of the matrix are polyorganosiloxanes comprising units of formula (IV) terminated by units of formula (V) or are cyclic polyorganosiloxanes comprising units of formula (IV):

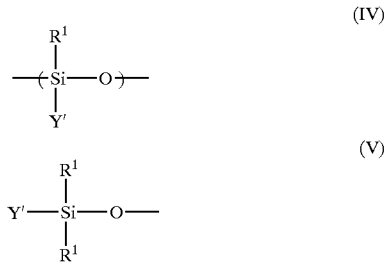

wherein:
R¹ is the same or different and represents:
a linear or branched alkyl radical having 1 to 8 carbon atoms which is optionally substituted by at least one halogen,
an optionally substituted cycloalkyl radical comprising between 5 and 8 cyclic carbon atoms,
an aryl radical comprising between 6 and 12 carbon atoms which can be substituted, or
an aralkyl radical having an alkyl part comprising between 5 and 14 carbon atoms and an aryl part comprising between 6 and 12 carbon atoms, which is optionally substituted on the aryl part by halogens, alkyls or alkoxyl groups comprising 1 to 3 carbon atoms, Y' is the same or different and represents:
the R¹ group,
a hydrogen radical, or
a crosslinkable organofunctional group, bonded to the silicon of the polyorganosiloxane via a divalent radical comprising from 2 to 20 carbon atoms, optionally bearing at least one heteroatom, and
at least one of the Y' symbols represents a crosslinkable functional organic group.

11. A resin obtained from the compositions defined in claim 9.

12. A coating comprising a resin as claimed in claim 11.

13. A coating according to claim 12, wherein the coating is a varnish, an adhesive coating, a nonstick coating or an ink.

* * * * *